US012728047B2

(12) United States Patent
Nakahata et al.

(10) Patent No.: US 12,728,047 B2
(45) Date of Patent: Sep. 8, 2026

(54) ABSORBENT ARTICLE HAVING FASTENING SYSTEM

(71) Applicant: The Procter & Gamble Company, Cincinnati, OH (US)

(72) Inventors: Hiroshi Nakahata, Cincinnati, OH (US); Urmish Popatlal Dalal, Milford, OH (US); James David Landgrebe, Madeira, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 725 days.

(21) Appl. No.: 18/102,964

(22) Filed: Jan. 30, 2023

(65) Prior Publication Data

US 2023/0240915 A1 Aug. 3, 2023

Related U.S. Application Data

(60) Provisional application No. 63/304,755, filed on Jan. 31, 2022.

(51) Int. Cl.
*A61F 13/15* (2006.01)
*A61F 13/62* (2006.01)
*A61F 13/58* (2006.01)

(52) U.S. Cl.
CPC .......... *A61F 13/622* (2013.01); *A61F 13/625* (2013.01); *A61F 13/581* (2013.01); *A61F 13/62* (2013.01)

(58) Field of Classification Search
CPC ...... A61F 13/581; A61F 13/62; A61F 13/625; A61F 13/622
USPC .......................................................... 604/391
See application file for complete search history.

(56) References Cited

U.S. PATENT DOCUMENTS 537,722 A 4/1895 Sander
5,782,819 A * 7/1998 Tanzer .............. A61F 13/15203 2/337
8,496,640 B2 7/2013 Molander
8,784,722 B2 7/2014 Rocha
10,076,162 B2 9/2018 Rocha
10,798,997 B2 10/2020 Rocha
2002/0078536 A1 6/2002 Martin et al.
2003/0100878 A1* 5/2003 Leak ..................... A61F 13/622 604/386
2004/0243091 A1* 12/2004 Mitsui .................. A61F 13/625 604/389
2007/0073260 A1 3/2007 Roe (Continued)

FOREIGN PATENT DOCUMENTS

CA 2348464 A1 5/2000

OTHER PUBLICATIONS

15858 PCT Search Report and Written Opinion for PCT/US2023/061411 dated Jun. 13, 2023, 16 pages.

*Primary Examiner* — Jacqueline F Stephens
(74) *Attorney, Agent, or Firm* — Gregory P. Habiak; Sarah M. DeCristofaro

(57) ABSTRACT

A fastening member includes a base substrate and one or more engagement portions disposed on the base substrate. The one or more engagement portions comprise a first engagement portion. The engagement portions each comprise one or more hooks. The fastening member comprises a fold line and the fold line is at least partially disposed within the first engagement portion.

18 Claims, 12 Drawing Sheets

(56) References Cited

U.S. PATENT DOCUMENTS

| | | | |
|---|---|---|---|
| 2017/0354553 | A1* | 12/2017 | Peltier .................. A61F 13/622 |
| 2020/0179184 | A1 | 6/2020 | Kaiser |
| 2021/0145661 | A1 | 5/2021 | Surushe et al. |
| 2021/0145662 | A1 | 5/2021 | Hayden et al. |
| 2021/0145663 | A1 | 5/2021 | Hayden et al. |

* cited by examiner

ABSORBENT ARTICLE HAVING FASTENING SYSTEM

FIELD OF THE INVENTION

The present disclosure relates to absorbent articles having fastening systems.

BACKGROUND OF THE INVENTION

It has long been known that absorbent articles such as conventional absorbent articles (e.g., diapers, adult incontinence articles) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer. Fastening systems have been used to ensure the article is secured about the wearer and remains in place. One popular configuration of absorbent article with a fastening system includes an absorbent chassis having a front waist region, crotch region and rear waist region, with a pair of fastening members each extending respectively laterally from left and right longitudinal edges of the chassis in the rear waist region. Such fastening members may be folded and lightly attached to an ear or the chassis, or may be covered with a release paper, to protect fastening elements from insult and/or contamination prior to intended use. Given the need to protect the fastening elements, regions of fastening elements are often narrow, particularly non-adhesive, mechanical fastening elements. Indeed, in typical folded configurations, the fastening member's foldline is disposed outside of the region of fastening elements, as the fastening element region is often too stiff to permit folding. Likewise, the fastening member is often attached to the chassis or other component of the article away from the fastening element region, as the fastening element region may be too stiff and/or fastening element material maybe insufficient to permit permanent suitable attachment to the chassis. Further, in typical configurations having release papers, it is desirable to minimize the amount of extra material necessary. Therefore, fastening element regions may be made as narrow as possible to minimize the amount of release paper utilized.

In narrowing the fastening element region, however, manufacturers create additional challenges. Fewer fastening elements may result in less adhesion or may require stronger, more expensive types of fastening elements than could be used if a greater fastening area were utilized. Therefore, there is a need for a fastening element area that provides sufficient adhesion in an efficient and cost effective manner. There is also a need for fastening elements that do not adversely interfere with mechanisms that protect the fastening elements from insult prior to use and/or with attachment of the fastener to another component of the article.

SUMMARY OF THE INVENTION

The invention comprises the features of the independent claims herein. A fastening member comprises a base substrate and one or more engagement portions disposed on the base substrate. The one or more engagement portions comprise a first engagement portion. The engagement portions each comprise one or more hooks, the fastening member comprises a fold line, and the fold line is at least partially disposed within the first engagement portion.

A fastening member comprises a base substrate having a first outboard longitudinal edge and a first inboard longitudinal edge; and an engagement portion disposed on the base substrate. The engagement portion comprises a second outboard longitudinal edge and a second inboard longitudinal edge. The first outboard longitudinal edge is at least partially coincident with the second outboard longitudinal edge and the first inboard longitudinal edge is at least partially coincident with the second inboard longitudinal edge.

An absorbent article comprises a topsheet, backsheet and absorbent core disposed between the topsheet and backsheet, and further comprising a back ear and a fastening member. The fastening member comprises a base substrate having an engagement portion disposed thereon, wherein the fastening member is joined to the back ear at a fastener attachment bond; and wherein the fastener attachment bond is at least partially disposed in the engagement portion.

A method of forming fastening members comprises the steps of: providing a web of base substrate material; disposing one or more engagement portions on the web of base substrate material to form a strip of fastening members, each engagement portion comprising a plurality of fastening elements; and cutting the strip of fastening members in at least one engagement portion such that a cut separates two fastening members, the two fastening members each comprising a final engagement portion that extends a full width of the fastening member.

A method of forming fastening members comprises the steps of: providing a web of base substrate material; disposing a plurality of engagement portions on the web of substrate material to form a strip of fastening members, each engagement portion having a first transverse edge and a second transverse edge and a plurality of fastening elements; and cutting the strip of fastening members between the first and second transverse edges of a leading engagement portion and cutting the strip between the first and second transverse edges of a trailing engagement to form fastening members each having one or more final engagement portions and an exposed substrate portion.

A method of assembling a fastening member on an absorbent article comprises the steps of: providing an absorbent article component; providing a fastening member comprising a base substrate and one or more engagement portions disposed on the base substrate, each engagement portion comprising one or more fastening elements; and attaching the fastening member to the absorbent article component in at least one engagement portion to form a composite.

DETAILED DESCRIPTION OF THE INVENTION

Figure 1:
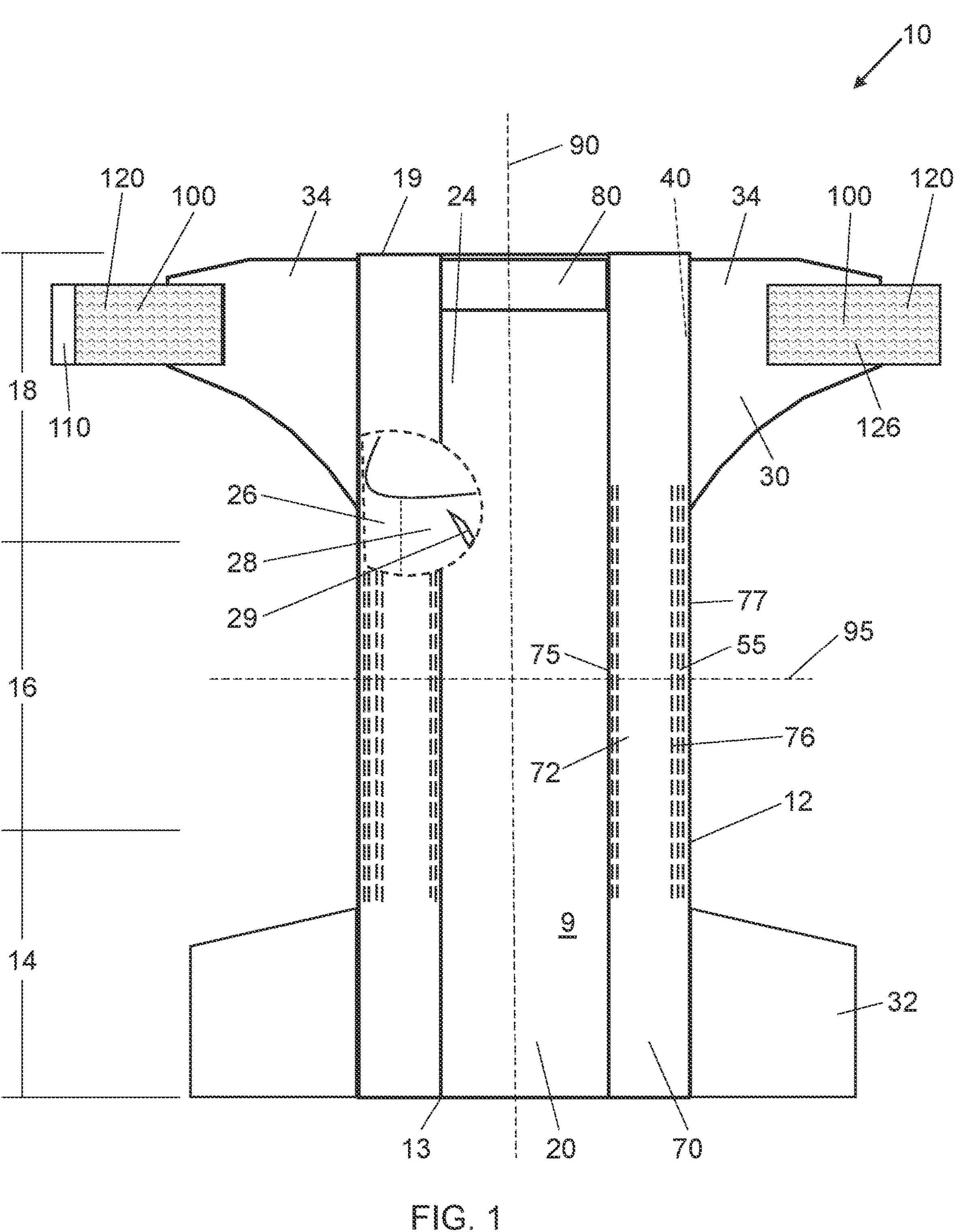
FIG. 1 is a schematic plan view of an exemplary absorbent article according to one nonlimiting embodiment of the present invention. The absorbent article is shown in a flat, uncontracted state.

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Disposable," in reference to articles, means that the articles are generally not intended to be laundered or otherwise restored or reused in the same capacity (i.e., they are intended to be discarded after a single use and, preferably, to be recycled, composted or otherwise discarded in an environmentally compatible manner).

"Disposed" refers to an element being located in a particular place or position. A feature that is disposed on a surface or side of a component may be integral with said component or may be joined to said component.

"Inboard," with respect to a first feature of an article and its position relative a second feature or location on the article, means that the first feature lies closer to a respective axis of the article than the second feature or location, along a horizontal x-y plane approximately occupied by the article when laid out flat, extended to the full longitudinal and lateral dimensions of its component web materials against any contraction induced by any included pre-strained elastomeric material, on a horizontal surface. Laterally inboard means the first feature is closer to the longitudinal axis, and longitudinally inboard means the first feature is closer to the lateral axis. Conversely, "outboard," with respect to a first feature of an article and its position relative a second feature or location on the article, means that the first feature lies farther from the respective axis of the article than the second feature or location.

"Integral" means configurations whereby an element is created from or created by an article component, or portions thereof, as opposed to being joined to the component. "Integrally formed" means an element is created from an underlying material or portion thereof, by for example molding, shaping and/or reconstituting the material.

"Longitudinal" means a direction lengthwise in a component such that the longitudinal direction runs parallel to the maximum linear dimension in the x-y plane of the component. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article.

"Lateral" refers to a direction generally perpendicular to the longitudinal direction. In the absorbent article described herein, the lateral direction runs substantially parallel from a side edge to an opposing side edge.

"Machine direction" (MD) refers to the direction of material flow through a process. In addition, relative placement and movement of material can be described as flowing in the machine direction through a process from upstream in the process to downstream in the process.

"Cross direction" (CD) refers to a direction that is generally perpendicular to the machine direction.

Overview

FIG. 1 is a plan view of an exemplary, nonlimiting embodiment of an absorbent article 10. The absorbent article comprises a fastening member 100. The fastening member 100 comprises a base substrate 110 and an engaging portion 120 disposed on the base substrate 110. The engaging portion 120 comprises one or more fastening elements 126. In various implementations, the fastening elements 126 may be mechanical fastening elements, including for example hooks 124. The fastening elements may be integral with the base substrate. The engagement portion 120 is operatively engageable with a receiving component 130, for example to secure the article about the waist of the wearer. The engagement portion may be disposed on the base substrate to a greater extent than known fastening members. The base substrate is foldable in the engagement portion and/or one or both longitudinal edges of the engagement portion are at least partially coincident with the longitudinal edge(s) of the substrate. Additionally, or alternatively, the engagement portion at least partially overlaps the area where the fastening member is joined to the ear or other chassis. These and other features will be described in more detail below.

Absorbent Article

Returning to FIG. 1, the absorbent article 10 includes a longitudinal centerline 90 and a lateral centerline 95. The outer periphery of the chassis 20 is defined by longitudinal edges 12 and waist edges (first waist edge 13 in first waist region 14 and second waist edge 19 in second waist region 18). The chassis 20 may have opposing longitudinal edges 12 that are oriented generally parallel to the longitudinal centerline 90. However, for better fit, longitudinal edges 12 may be curved or angled to produce, for example, an "hourglass" shape article when viewed in a plan view as shown in FIG. 1. The chassis 20 may have opposing lateral edges 13, 19 (i.e., the first waist edge 13 and second waist edge 19) that are oriented generally parallel to the lateral centerline 95.

The chassis 20 may comprise a liquid permeable topsheet 24, a backsheet 26, and an absorbent core 28 between the topsheet 24 and the backsheet 26. The absorbent core may comprise absorbent material, including for example superabsorbent particles and absorbent gelling materials (AGM). The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 27 is disposed between the topsheet 24 and the absorbent core 28.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Components of the disposable absorbent article can at least partially be comprised of bio-sourced content as described in U.S. Pat. Pub. Nos. 2007/0219521A1, 2011/0139658A1, 2011/0139657A1, 2011/0152812A1, and 2011/0139659A1. These components include, but are not limited to, topsheets, backsheet films, backsheet nonwovens, side panels/ears, leg gasketing systems, superabsorbent, acquisition layers, core wrap materials, adhesives, fastener systems, and landing zones. In at least one embodiment, a disposable absorbent article component comprises a bio-based content value from about 10% to about 100%, or from about 25% to about 75%, or from about 50% to about 60% using ASTM D6866-10, method B. In order to apply the methodology of ASTM D6866-10 to determine the bio-based content of any component, a representative sample of the component must be obtained for testing. In at least one embodiment, the disposable absorbent article component can be ground into particulates less than about 20 mesh using known grinding methods (e.g., WILEY® mill), and a representative sample of suitable mass taken from the randomly mixed particles.

Topsheet

The topsheet 24 is generally a portion of the absorbent article 10 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. The topsheet 24 may be apertured. The topsheet may be apertured by overbonding a material and then rupturing the overbonds through ring rolling, such as disclosed in U.S. Pat. No. 5,628,097.

Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Aborbent Core

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels 29, wherein said channels are substantially free of absorbent particulate polymer material. The channels 29 may extend longitudinally or laterally. The absorbent core may further comprise two or more channels. The channels may be straight, curvilinear, angled or any workable combination thereof. In nonlimiting examples, two channels are symmetrically disposed about the longitudinal axis.

Backsheet

The backsheet 26 is generally positioned such that it may be at least a portion of the garment-facing surface of the absorbent article 10. The backsheet 26 may be joined to portions of the topsheet 24, the absorbent core 28, and/or any other layers of the absorbent article by any attachment methods known to those of skill in the art. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Backsheet 26 may also consist of more than one layer. The backsheet 26 may comprise an outer cover and an inner layer. The outer cover material may comprise a bond pattern, apertures, and/or three-dimensional features. The outer cover material may be a nonwoven material, such as a hydroentangled nonwoven material.

Ears

The absorbent article 10 may include one or more ears 30, including for example front ears 32 disposed in the first waist region and/or back ears 34 disposed in the second waist region. The ears 30 may be integral with the chassis or discrete elements joined to the chassis 20 at a chassis attachment bond 40, which may join one or more layers of the ear to the chassis. The ears 30 may be extensible or elastic. The ears 30 may be formed from one or more nonwoven webs, woven webs, knitted fabrics, polymeric and elastomeric films, apertured films, sponges, foams, scrims, or combinations and/or laminates of any the foregoing.

In some embodiments, the ear 30 may include elastomers, such that the ear is stretchable. In certain embodiments, the ears 30 may be formed of a stretch laminate such as a nonwoven/elastomeric material laminate or a nonwoven/elastomeric material/nonwoven laminate, which also results in the ear being stretchable. The ear 30 may be extensible in the lateral direction of the article. In some embodiments, the ear is elastic in the lateral direction. In further embodiments, the ear 30 may be more extensible in the lateral direction than in the longitudinal direction. Alternatively, the ear may be more extensible in the longitudinal direction than in the lateral direction. In certain nonlimiting examples, the ear may include one or more inelastic regions along with a separate elastic region. The chassis attachment bond may be located in an inelastic region.

Any suitable nonwoven may be used in an ear 30. Suitable nonwovens may comprise a basis weight of at least about 8 gsm, or less than about 22 gsm, or about 17 gsm or less, or from about 10 gsm to about 17 gsm, reciting for said range every 1 increment therein. Typically, lower basis weight nonwovens reduce an ear's overall strength. Where the ear 30 comprises more than one nonwoven, the nonwovens may comprise the same basis weight or different basis weights. Likewise, the nonwovens may comprise the same layer structure or different layer structures. Further, a nonwoven in the ear may comprise the same or different features of nonwovens in the backsheet, topsheet, leg gasketing system and/or waist feature.

The ear may comprise an ultrasonically bonded ear as is disclosed for example in U.S. patent. application Ser. No. 15/674,559. The ear may be a gathered laminate 24. Alternatively, the ear may be activated by processes disclosed in U.S. Pat. Pub. No. 2013/0082418, U.S. Pat. Nos. 5,167,897; 5,993,432; 5,156,793; 5,167,897; 7,062,983 and 6,843,134 for example.

Fastening Members

Figure 1A:
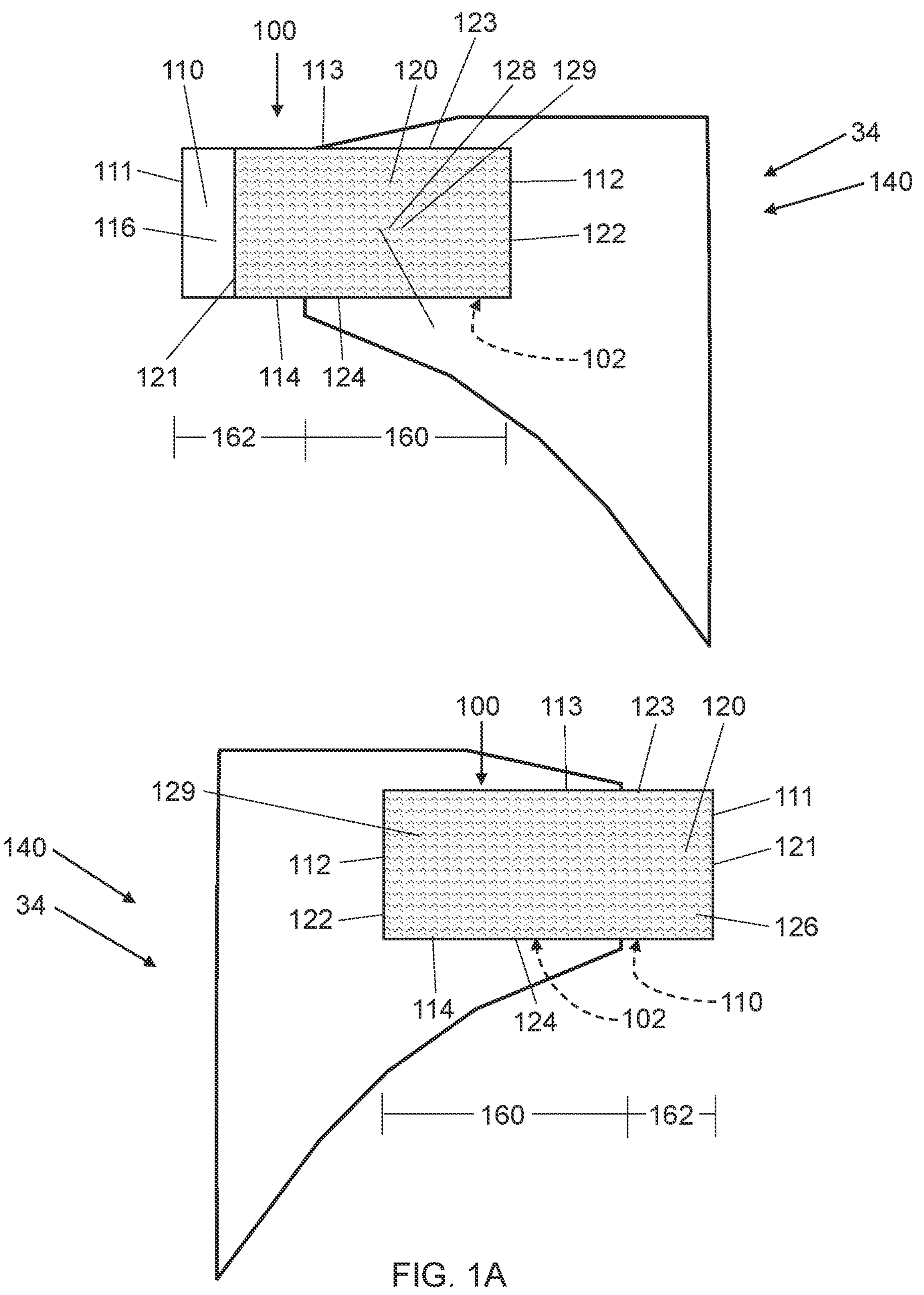
FIG. 1A is a schematic plan views of exemplary ears having exemplary fastening members according to a nonlimiting embodiment of the present invention.

As shown in FIGS. 1-1A, the absorbent article 10 also includes a fastening member 100. The fastening member 100 is used to attach one portion of the article to itself and/or to another portion of the article. For example, fastening members 100 are typically used to connect the first waist region 14 and the second waist region 18. While shown in the second waist region, it is also contemplated that a fastening member may be disposed in the front waist region. Further, a fastening member may be disposed in any portion of the article, which may facilitate closing or wrapping the article during disposal, securing the article to itself and/or securing the article to another surface such as a garment. The fastening member may be discrete from and joined to, or may be integral with, an article component 140. Suitable article components upon which a fastening member may be disposed include topsheets, backsheet films, backsheet nonwovens, side panels/ears, belts, leg gasketing systems, landing zones and combinations thereof.

Figure 2:
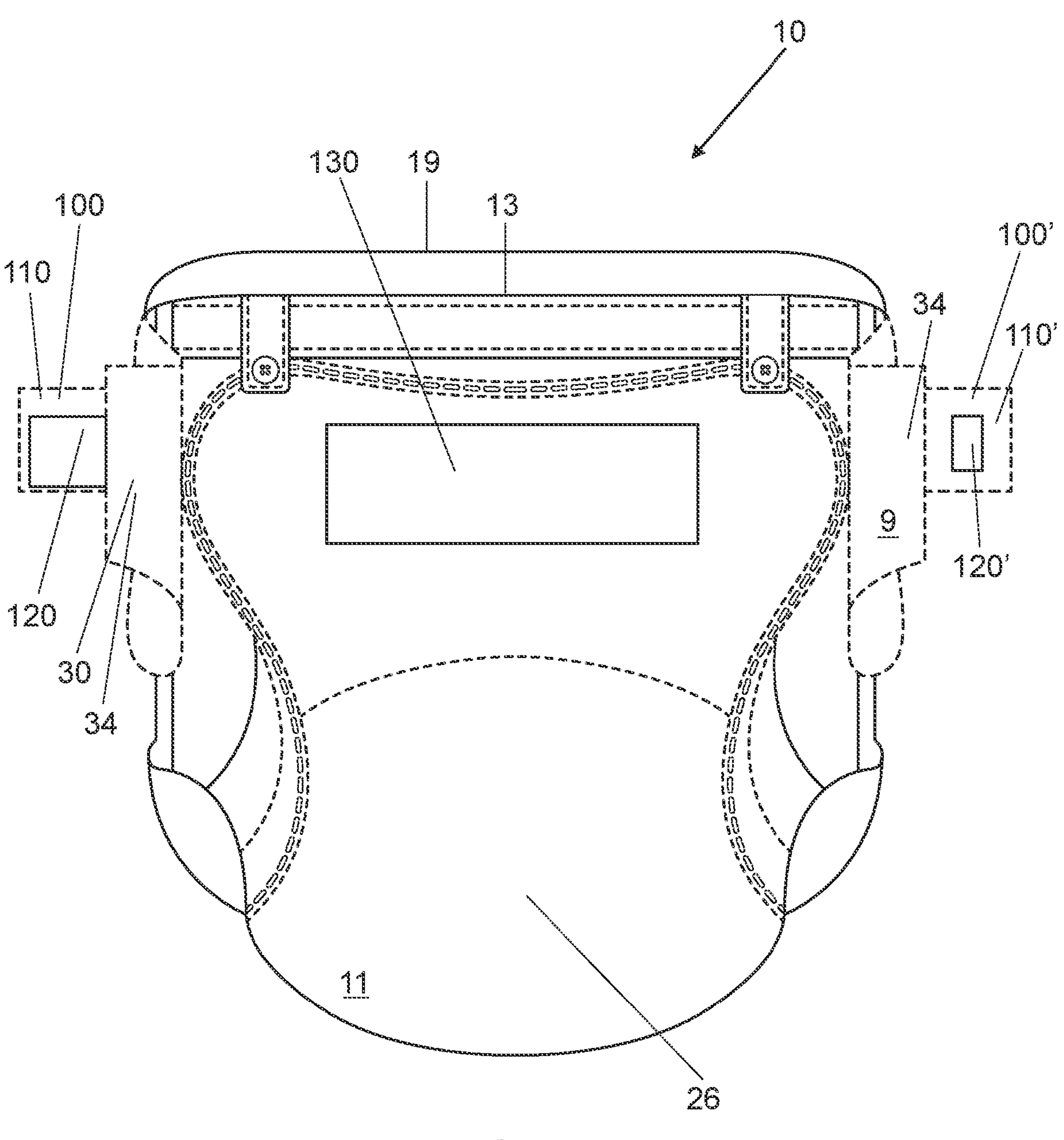
FIG. 2 is a schematic front elevation view of an exemplary absorbent article according to a nonlimiting embodiment. The absorbent article is shown in a folded state.

The fastening member 100 includes a base substrate 110 and an engagement portion 120. The engagement portion comprises one or more fastening elements 126, which cause the fastening member to join with another surface, such as a receiving component 130 as shown in FIG. 2. Receiving components comprise material adapted to operatively cooperate with fastening elements. Nonlimiting examples of engageable fastening elements and receiving components include tape tabs, hook and loop fastening components, interlocking fasteners such as tabs & slots, buckles, buttons, snaps, and/or hermaphroditic fastening components. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening element and/or the receiving component may further include a release tape or other material, including folded material, that protects the component from insult prior to use.

Figure 3:
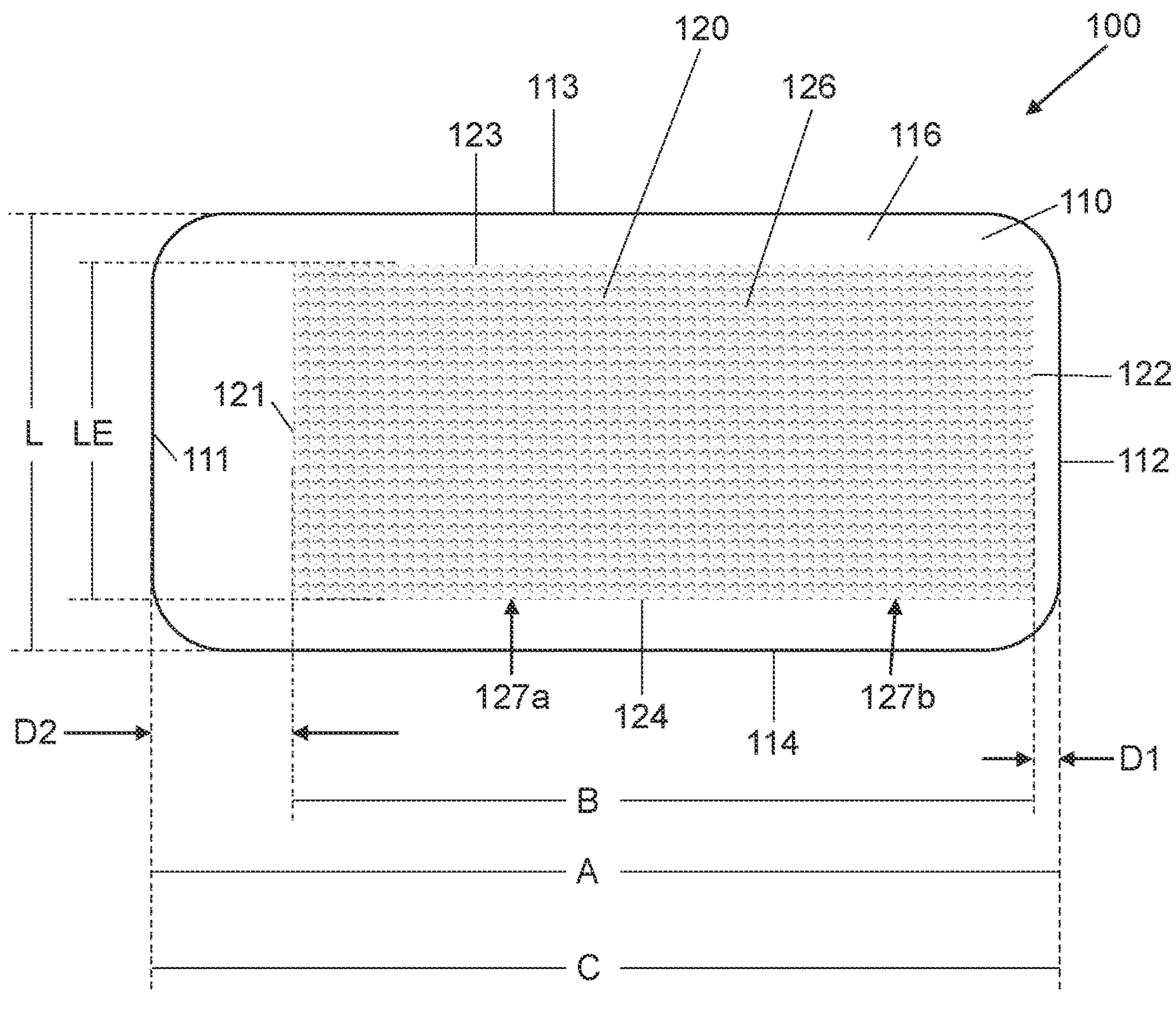
FIG. 3 is a schematic plan view of an exemplary fastening member according to a nonlimiting embodiment of the present invention.

The base substrate may comprise a nonwoven, a film or combinations thereof. Such materials may be formed from one or more polyolefins, polyester, nylon and combinations thereof. Returning to FIG. 1A, the base substrate comprises a first outboard longitudinal edge 111, a first inboard longitudinal edge width 112, a first outboard lateral edge 113 and a first inboard lateral edge 114. The base substrate may be integral with an article component 140, such as the chassis, an ear, or another article component. Alternatively, the base substrate may be discrete from the chassis and/or ear and joined thereto, or to another article component 140, via a fastener attachment bond 102. In such embodiments, the base substrate may be joined to the article component on a wearer-facing side, on a garment-facing side, or between layers of the component. For example, the base substrate may be joined to the wearer-facing surface of the backsheet, topsheet or ear. Alternatively, the base substrate may be joined to the garment-facing surface of the backsheet or ear. As another alternative, the base substrate may be joined between layers of an ear (e.g., between two nonwoven layers or between a nonwoven layer and a film layer). Turning to FIG. 3, the base substrate comprises a base maximum width, A, extending between the longitudinal edges 111, 112 and a base maximum length, L, extending between the lateral edges 113, 114. Further, the base substrate comprises a base area inside the periphery defined by its edges (i.e., the two-dimensional area). The area is calculated by known geometric calculations.

Figure 4A:
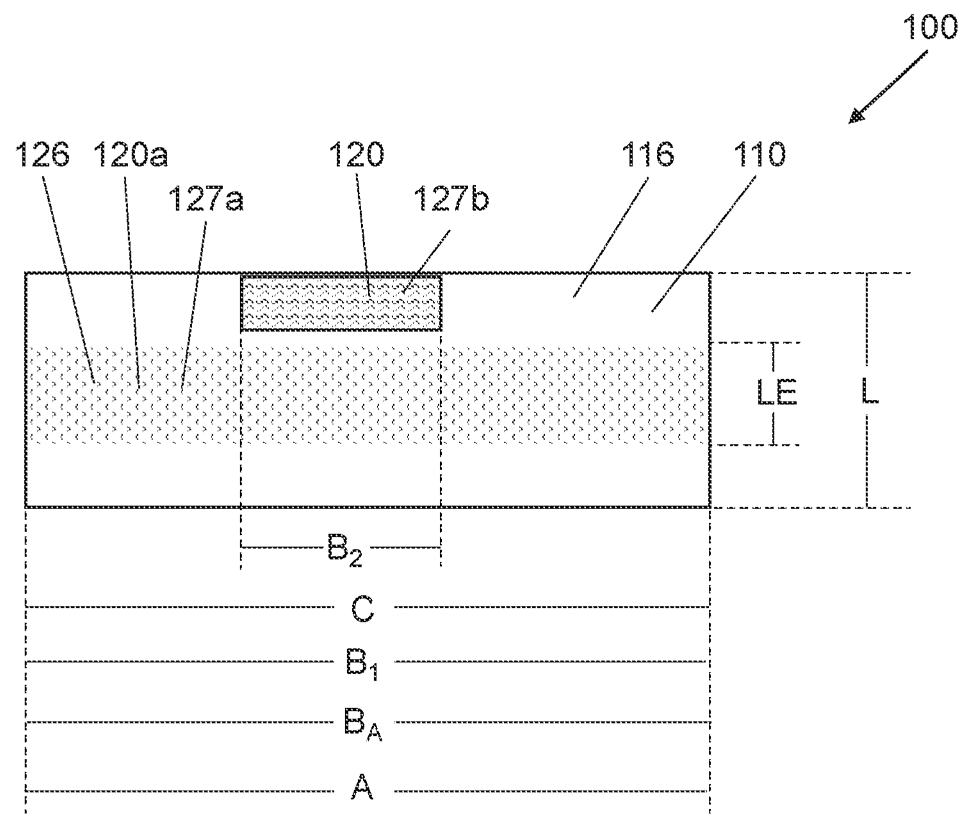
FIGS. 4A-4B are schematic plan views of a fastening members according to nonlimiting embodiments of the present invention.
Figure 4B:
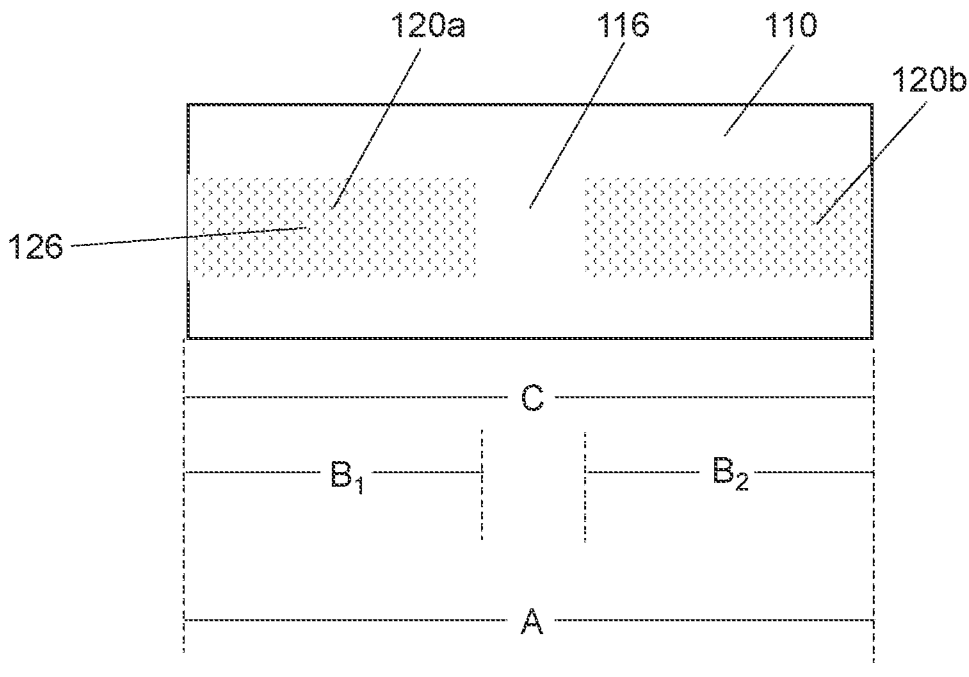

Still referring to FIG. 3, the fastening member further comprises one or more engagement portions 120, having one or more fastening elements 126. An engagement portion comprises a second outboard longitudinal edge 121, a second inboard longitudinal edge 122, a second outboard lateral edge 123 and a second inboard lateral edge 124. The engagement portion has an engagement maximum width, B, extending between its longitudinal edges 121, 122 and an engagement maximum length, LE, extending between its lateral edges 123, 124. The engagement portion further comprises an engagement area inside the periphery defined by its edges. The area is calculated using known geometric calculations for two-dimensional areas. The engagement maximum width, B, may be at least 18 mm. Additionally, or alternatively, the engagement maximum width, B, be at least 50%, or at least 70%, or at least 90%, or 100%, or from 50% to 100% of the base maximum width, A. Further, the engagement area may be at least 50%, or at least 60%, or at least 75%, or 100%, or from 50% to 100% of the base area, reciting for said range every 5% increment therein.

Where the fastening member comprises more than one engagement portion (e.g., a first engagement portion 120*a* and a second engagement portion 120*b* as shown in FIGS. 4A-4B), the dimensions of the engagement portions may be the same or may differ. The engagement portions may collectively comprise an aggregate maximum width, $B_A$, which is calculated by adding the maximum width of each engagement portion and subtracting any overlapping portions from the sum. Therefore, the aggregate maximum width, $B_A$, in FIG. 4A is equivalent to the engagement maximum width, $B_1$, of the wider of the two engagement portions (i.e., the first engagement portion 120*a*). In FIG. 4B, the aggregate maximum width, $B_A$, is the sum of the widths $B_1$, $B_2$ of the two portions, as there is no overlapping area. Likewise, multiple engagement portions may comprise an aggregate engagement area, which is the sum of their individual two-dimensional areas. The aggregate engagement maximum width, $B_A$, may be at least 18 mm. Additionally, or alternatively, the engagement maximum width, $B_A$, be at least 50%, or at least 70%, or at least 90%, or 100%, or from 50% to 100% of the base maximum width, A. Further, the aggregate engagement area, $B_A$, may be at least 50%, or at least 60%, or at least 75%, or 100%, or from 50% to 100% of the base area, reciting for said range every 5% increment therein.

Returning to FIG. 3, at least one engagement portion may comprise a second longitudinal inboard edge 122 that is separated from the first inboard edge 112 by a maximum distance, D1, of about 5 mm or less, or about 3 mm or less, or from about 0 mm to about 5 mm, or from about 1 mm to about 4 mm, reciting for each range every 0.5 mm increment therein. Additionally, or alternatively, at least one engagement portion may have a longitudinal outboard edge 121 that is separated from the first longitudinal outboard edge 111 by a maximum distance, D2, of about 5 mm or less, or about 3 mm or less, or from about 0 mm to about 5 mm, or from about 1 mm to about 4 mm, reciting for each range every 0.5 mm increment therein. The maximum separation, D2, may be about 10% or less, or about 5% or less, or from about 0% to about 10%, or from about 2% to about 5% of the base maximum distance, A.

The fastening member may comprise an exposed portion 116, wherein the base substrate void of fastening elements. The fastening member is not capable of engaging with a receiving component in the exposed portion 116. The exposed portion 116 may separate engagement portions and/or surround engagement portion(s). The exposed portion 116 comprises an exposed portion maximum width, C, and an exposed portion area as calculated by using known geometric calculations for two-dimensional areas. The engagement maximum width, B, and/or the aggregate engagement maximum width, $B_A$, may be greater than exposed portion maximum width, C. The engagement maximum width, B, and/or the aggregate engagement maximum width, $B_A$, may be at least about 20%, or at least about 40%, or at least about 50%, or from about 20% to about 200% greater than the third maximum width. The percent difference is calculated by subtracting the exposed portion maximum width from the engagement maximum width and dividing the difference by the exposed portion maximum width and multiplying by 100%.

The exposed portion may be continuous as shown in the fastening member in FIG. 3 for example or discontinuous as shown in FIG. 4A for example. Where the exposed portion is discontinuous, the maximum width, C, can be determined by adding nonoverlapping lateral widths. Additionally, or alternatively, the engagement area (i.e., the area of the engagement portion) and/or the aggregate engagement area may be greater than the area of the exposed area. The engagement area may be at least may be at least about 20%, or at least about 40%, or at least about 50%, or from about 20% to about 200% greater than the exposed portion area and/or the aggregate engagement area may be at least may be at least about 20%, or at least about 40%, or at least about 50%, or from about 20% to about 200% greater than the exposed portion area. The percent difference is calculated by subtracting the exposed portion area from the engagement area (or aggregate engagement area as applicable) and dividing the difference by the exposed portion area and multiplying by 100%.

In various embodiments, one or more edges of an engagement portion coincide with one or more edges of the base substrate. In such embodiments, the first outboard longitudinal edge at least partially coincides with the outboard longitudinal edge of an engagement portion and/or the first inboard longitudinal edge at least partially coincides with an inboard longitudinal edge of an engagement portion as is illustrated in FIGS. 4A-4B, for example. An engagement portion may extend the full width and/or full length of the base substrate in one or more areas. In nonlimiting examples, the engagement portion extends the full width of the base substrate throughout the entire length of the base substrate (as shown in FIG. 1 in the right fastening member) and/or throughout the entire length of the engagement portion (as shown in FIG. 4A). Additionally, or alternatively, the engagement portion extends the full length of the base substrate throughout the entire width of the engagement portion (e.g., FIG. 1A left fastening member) and/or throughout the entire width of the base substrate (e.g., the right fastening member on FIG. 1A).

By having one or more of the foregoing dimensions, a greater portion of the base substrate is available for engagement during fastening than known fasteners, thereby better securing the article about the wearer (or for other purposes). This is especially true when the base substrate is attached to a wearer-facing surface of an article component 140 (e.g., ear, backsheet), where none of the fastening elements are covered in the area of overlap between the base substrate and the article component as shown in FIG. 1. Further, it is believed that by spreading fastening elements over a greater surface, tensile forces can be deconcentrated and the fastening member is less likely to rotate when fastened.

The engagement portion 120 may comprise the same material as the base substrate or different materials. Nonlimiting examples of suitable materials include nonwovens, films and combinations thereof. Such materials may be formed from one or more polyolefins, polyester, nylon and combinations thereof. The engagement portion comprises fastening elements. Nonlimiting examples of fastening elements include tabs, buckles, snaps, buttons, male components in hermaphroditic systems, and hooks 128. The fastening elements are preferably non-adhesive, mechanical elements.

Figures 5A, 5B, 5C:
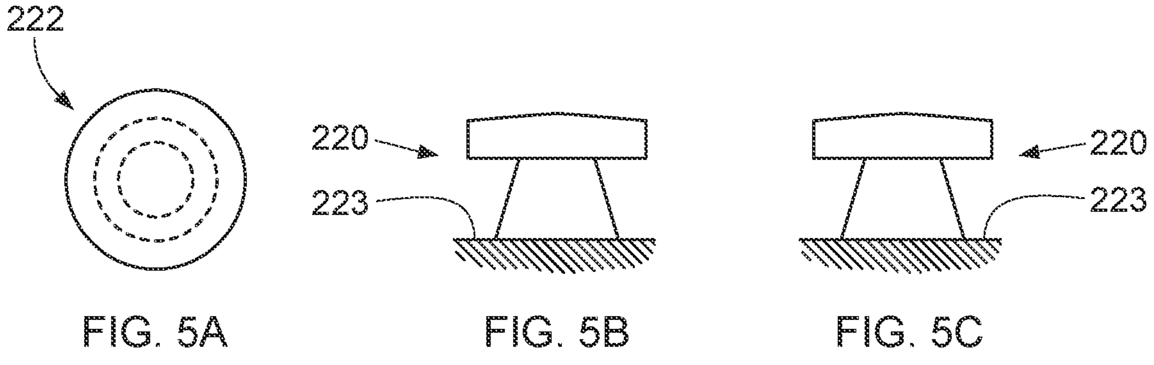
FIGS. 5A-5C, 6A-6C, and 7A-7C depict front, side and top views of examples of profiles of hooks protruding from a substrate.
Figures 6A, 6B, 6C:
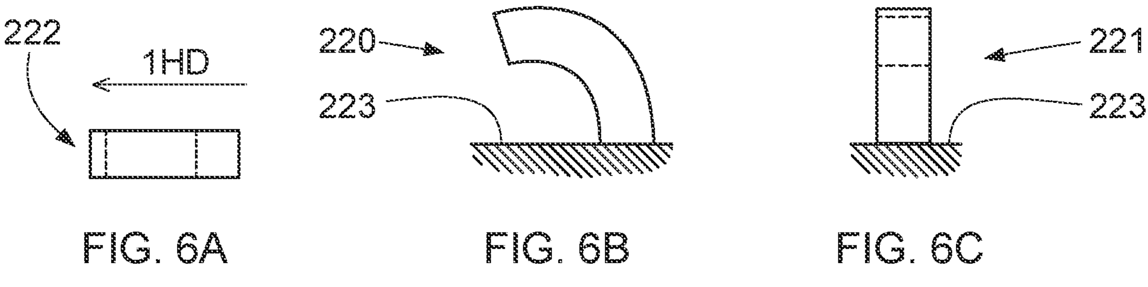
Figures 7A, 7B, 7C:
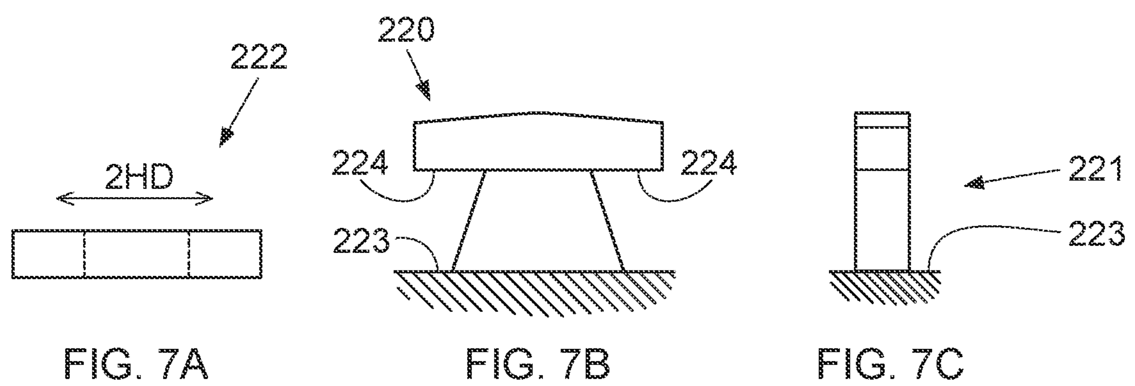

In various embodiments, the fastening elements comprise hooks 128. Exemplary hook shapes are shown in FIGS. 5A-7C. Each of FIGS. 5A-7C depicts a front view 220, side view 221 and top view 222 of one of three non-limiting examples of hook shapes, protruding or emerging from a base substrate 110. The hook shape example reflected in FIGS. 5A-5C is substantially unidirectional in that it hooks over predominately in one direction 1HD. Referring to FIGS. 6A-6C, this type of hook shape (sometimes described as a "mushroom" shape) lacks directionality because it is substantially symmetrical about all planes along its vertical (z-direction) axis and/or has substantially similar front and side view profiles. The hook shape reflected in FIGS. 7A-7C (sometimes described as an "arrowhead" shape) is substantially bi-directional in that it has two opposing arms 224 that hook over in two opposite directions 2HD.

Fastening elements may be discrete sections or patches of material that are bonded by heat, compression, adhesive, ultrasonic bonding or any combination thereof. The discrete material may be the same material as the base substrate or different materials. Nonlimiting examples of fastening element constituent material include polyethylene, polypropylene, polyester, nylon, and combinations thereof. In other examples, fastening elements may be patches of hooks that are formed directly on a section of the base substrate. For example, the fastening elements may be produced via application of molten polymer resin onto the layer, and subsequent formation of hooks in and from the melted, applied resin via known methods.

In certain embodiments, the fastening elements comprise integral fastening elements 129. Integral fastening elements 129 may be integrally formed from the base substrate by heating and softening a portion of the material and pressing it into forming cavities, as is disclosed in U.S. Pat. No. 8,784,722. The fastening elements may be integrally formed from the base substrate through a single continuous process as is disclosed in commonly assigned U.S. patent application Ser. No. 16/545,425. Further, integral fastening members may be formed from the base substrate and one or more additional layers as is disclosed in commonly assigned U.S. patent application Ser. No. 62/975,919. Layers and materials from which integral fastening elements may be formed may comprise a nonwoven, elastomer, film, polyolefin, adhesive, ink, dye, tactile modifier (e.g., silicone) and combinations thereof. A layer may be applied in a liquid state or in at least a partially molten state.

Fastening elements may differ in different areas of the fastening member. At least two fastening elements within an engagement portion may differ by one of the group consisting of: size, shape, directionality, whether the element is discrete or integral, constituent material, the number and/or type of layers from which integral fastening elements are formed, diameter, height and combinations thereof. Alternatively, fastening elements within an engagement portion may be substantially the same. Fastening elements may be disposed in two or more arrays 127*a*, 127*b* within one engagement portion as shown in FIG. 3, wherein the arrays differ by one of the group consisting of: peel strength, the number of fastening elements, shapes of fastening elements, directionality of fastening elements, orientation of array, average spacing of fastening elements, whether the elements are discrete or integral or some combination, fastening element constituent materials, the number and/or types of layers from which integral fastening elements are formed, average size of the fastening elements, average height of fastening elements, average fastening element diameter, aggregate shape of the array, surface area, opacity, color and combinations thereof. Additionally, or alternatively, different engagement portions may comprise differences in fastening elements as shown in FIG. 4A. Fastening elements in two different engagement portions may comprise arrays differing by one of the group consisting of: stiffness, peel strength, the number of fastening elements, shapes of fastening elements, directionality of fastening elements, orientation of array(s), average spacing of fastening elements, whether the elements are discrete or integral or some combination, fastening element constituent materials, the number and/or types of layers from which integral fastening elements are formed, average size of the fastening elements, average fastening element diameter, average fastening element height, aggregate shape of the array, surface area, opacity, color and combinations thereof. For instance, fastening elements comprising different diameters may be incorporated into a fastening element. Larger diameter fastening elements may be disposed near the outboard edge of engagement portion to provide stiffer, stronger fastening at the edge, while smaller diameter fastening elements could be disposed inboard. Additionally, or alternatively, shorter fastening elements may be disposed near a fold line (discussed below) to better enable folding while taller fastening elements may be disposed elsewhere to provider stronger engagement. Exemplary array configurations are disclosed in commonly assigned U.S. Patent App. No. 62/975,919.

Figure 8:
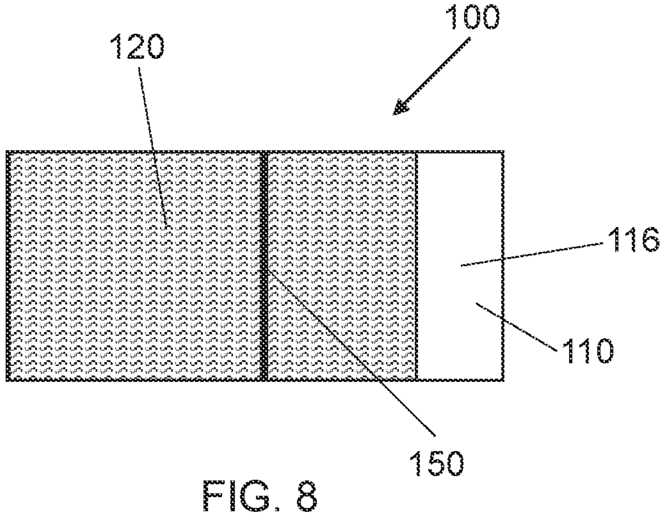
FIG. 8 is a schematic plan view of an exemplary fastening member according to a nonlimiting embodiment of the present invention.
Figure 9:
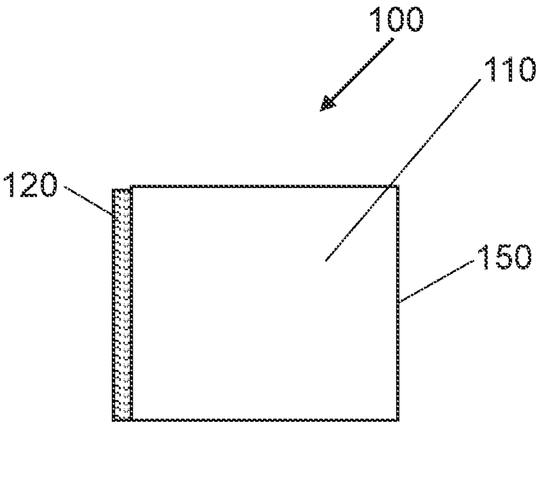
FIG. 9 is the fastening member of FIG. 8 in a folded state.

Turning to FIGS. 8 and 9, a fastening member comprises a fold line 150. As noted above, a fastening member may be folded about the fold line prior to use to cover one or more fastening elements and thereby protect the fastening elements from contamination or insult prior to use. Known fastening members provide fastening elements away from fold lines as the fastening elements tend to interfere with folding due to the stiffness from the fastening element materials. In the present invention, the fold line 150 may be at least partially disposed within the engagement portion, or even disposed fully within the engagement portion. Without being bound by theory, it is believed that the fastening member may be foldable within the engagement portion by integrally forming the fastening elements from the base substrate and thereby eliminating patches of additional materials and their related bulk and/or by providing a relatively low CD Stiffness to the engagement portion as disclosed below. By being foldable in the engagement portion, the fastening member can both protect fastening elements prior to insult and provide a greater surface area for fastening elements.

Additionally, or alternatively, in various embodiments, the fastener attachment bond 102 is at least partially disposed, or even fully disposed, within an engagement portion. Typically, fastening members are attached to the remainder of the absorbent article in an area free of fastening elements due to the stiffness and/or bulkiness of the fastening element material. By allowing the fastener attachment bond to disposed within the engagement portion, manufacturers are provided with a greater process window. Manufacturers are no longer required to position the fastening member or article component such that they are combined in an area outside of the engagement portion.

Returning to FIG. 1A, when attached to an absorbent article component 140, the fastening member comprises an overlapping zone 160 and a free zone 162. The fastening member overlaps the article component in the overlapping zone and does not overlap the article component in the free zone. In various embodiments, it is desired that a certain portion of the engagement portions be located within the overlapping zone in order to minimize curling and bending of the article component. In nonlimiting examples, the fastening member may comprise Overlap to Free Area Ratio is about 0.1 to about 1, as calculated by the ratio of the amount of aggregate engagement area that is located in the overlapping zone to the amount of aggregate engagement area that is disposed in the free zone.

One or more engagement portions may comprise CD Stiffness of about 600 N/m or less, or about 300 N/m or less or about 250 N/m or less, or from about 50 N/mm to about 600 N/m, or from about 100 N/mm to about 300 N/m, reciting for each range every 10 N/m increment therein, according to the 3-Point Bend Test Method herein. In nonlimiting examples, the ratio of CD Stiffness of the engagement portion to the CD Stiffness of the base substrate (outside of the engagement portion) may be 5 or less, or 3 or less, or 2 or less, or from 1 to 10, or from 1.5 to 5, reciting for each range every 0.5 increment therein. In such examples, the CD Stiffness of the engagement portion remains close to the CD Stiffness of the base substrate. Stated differently, the engagement portion does not substantially increase stiffness of the fastening member.

The receiving component may be discrete, such as a discrete patch of receiving material joined to the chassis or joined to another component that is attached to the chassis (e.g., an ear or belt) as shown in FIG. 2, for example. In other embodiments, the receiving component may be integral with the chassis or integral with another component joined to the chassis. In such embodiments, the backsheet, a belt, an ear 30 or combinations thereof may comprise material, such as nonwoven having loop material, which may form the receiving component.

The fastening member and the receiving component may each be any suitable shape or size. The engagement portion and the receiving component may be disposed on opposite surfaces of the article. For instance, the engagement portion may be disposed on the wearer-facing surface 9 of the article and the receiving component may be disposed on the garment-facing surface 11.

In certain embodiments, the article comprises multiple fastening members. The article may comprise two fastening members 100, 100' disposed in the second waist region and one or more receiving components 130 in the first waist region as is shown in FIG. 2. The fastening members 100, 100' may be the same or may differ by, for example, the number, size and/or shape of the engagement portions 120, 120'; size or shape of the base substrates 110, 110', types of fastening elements, directionality of fastening elements, whether the elements are discrete or integral or some combination, fastening element constituent materials (i.e., the material(s) from which the elements are made such as nonwoven, films and combinations thereof), the number and/or types of layers from which integral fastening elements are formed; stiffness; peel strength; the number of fastening elements; shapes of fastening elements; directionality of fastening elements; orientation of array(s); average spacing of fastening elements; average size of the fastening elements; average fastening element diameter; average fastening element height; aggregate shape of the array(s); surface area; opacity; color and combinations thereof.

Figure 10:
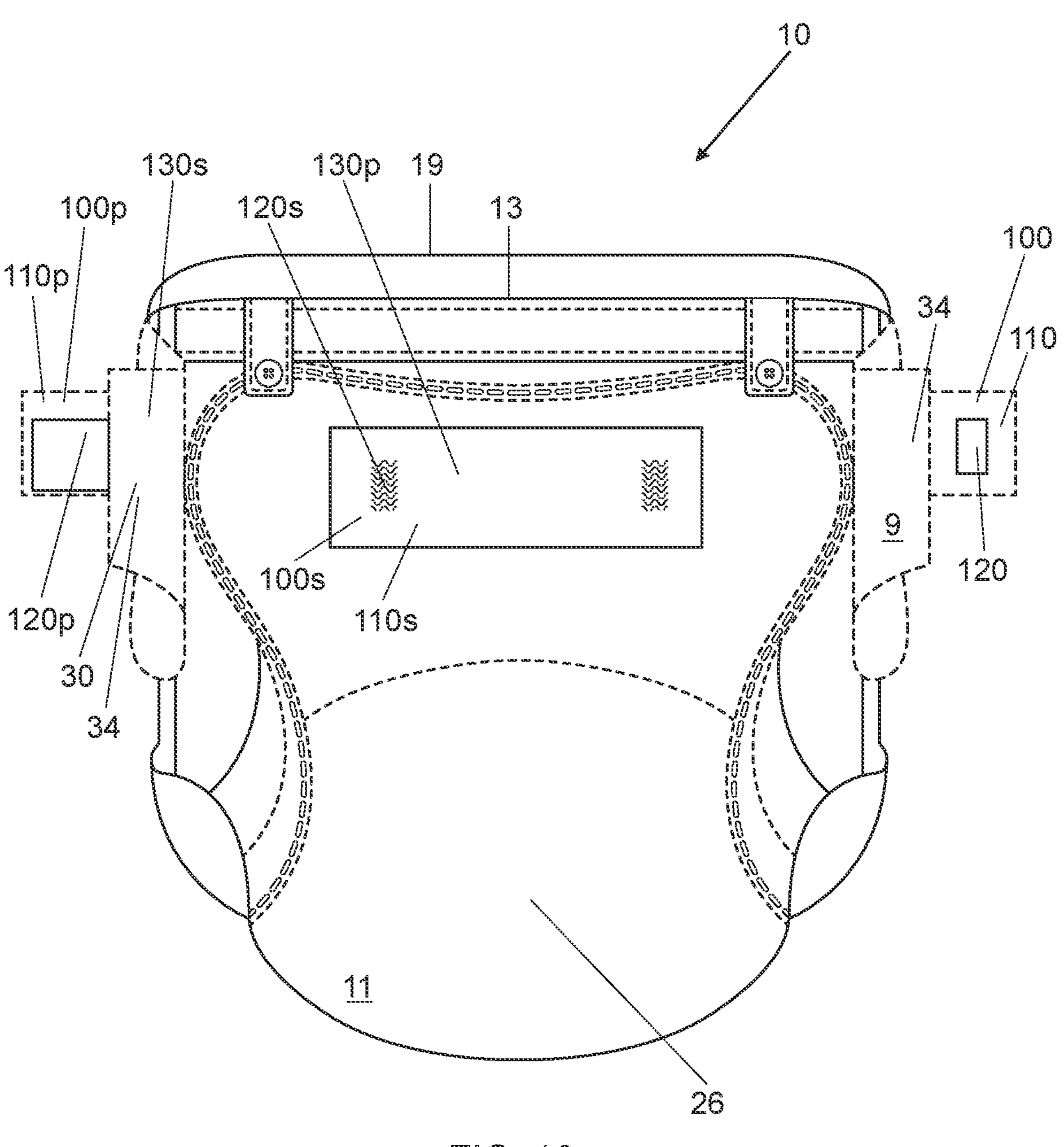
FIG. 10 is a schematic front elevation view of an exemplary absorbent article according to a nonlimiting embodiment. The absorbent article is shown in a folded state.

Additionally, or alternatively, the article may comprise a primary fastening member 100*p* and a secondary fastening member 100*s* disposed in different waist regions as shown in FIG. 10, in order to provide a greater surface area for fastening, and thereby de-concentrate lateral tensile forces communicated through the fastening location(s) as the rear waist region is pulled toward the front waist region, and vice versa, when the article is worn. The primary fastening member comprises one or more primary engagement portions 120*p* and primary base substrate 110*p*, and is disposed in the second waist region. The secondary fastening member 100*s* comprises one or more secondary engagement portions 120*s*, a secondary base substrate 110*s* and is disposed in the first waist region. The primary fastening member 120*p* is engageable with a primary receiving component 130*p* in the first waist region, and the secondary fastening member 120*s* is engageable with a secondary receiving component 130*s* in the second waist region. The fastening members 100*p*, 100*s* may be the same or may differ by, for example, size and/or shape of the engagement portions 120*p*, 120*s*, size or shape of the base substrates 110*p*, 110*s*, types of fastening elements, directionality of fastening elements, whether the elements are discrete or integral or some combination, fastening element constituent materials (i.e., the material(s) from which the elements are made such as nonwoven, films and combinations thereof), the number and/or types of layers from which integral fastening elements are formed, stiffness, peel strength, the number of fastening elements, shapes of fastening elements, orientation of array(s), average spacing of fastening elements, average size of the fastening elements, average fastening element diameter, average fastening element height, aggregate shape of the array(s), surface area, opacity, color and combinations thereof and combinations thereof. Likewise, the receiving components may be the same or may differ in size, shape and/or material. In nonlimiting examples, a receiving component may also serve as the base substrate for a fastening member having an engagement portion disposed thereon as shown in FIG. 10. For instance, a patch of loops material (i.e., a receiving component) may have hooks formed thereon or attached thereto as disclosed for example in U.S. patent application Ser. No. 16/685,230. As shown in FIG. 10, the article may include a third fastening member 100 which may have any of the features described above. It is also contemplated that the article comprise more than three fastening members, each having any of the above described features.

Methods of Forming Fastening Members/Assembling

Figure 11:
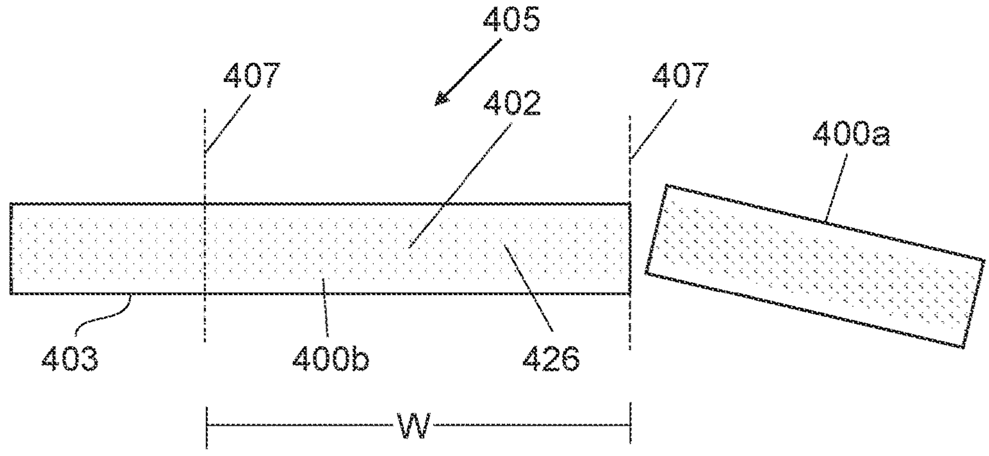
FIG. 11-12C are schematic plan views of an exemplary strips of fastening members according to nonlimiting embodiments of the present invention.

Turning to FIG. 11, a method to form fastening members of the present invention comprises providing a web of base substrate material 403, disposing one or more engagement portions 402 on the web of base substrate material to form a strip 405 of fastening members, and cutting the strip of fastening members in at least one engagement portion such that a cut 407 separates two fastening members 400*a*, 400*b*. The engagement portion comprise a plurality of fastening elements 426 having any of the features described above. The two fastening members each comprise a final engagement portion 420 that extends a full width, W, of the fastening member.

Figure 12A:
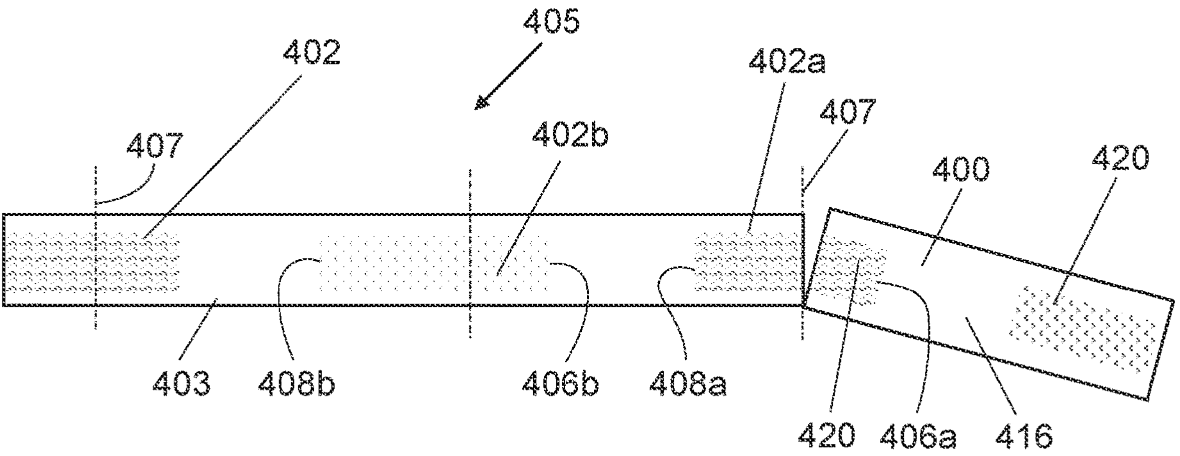
Figure 12B:
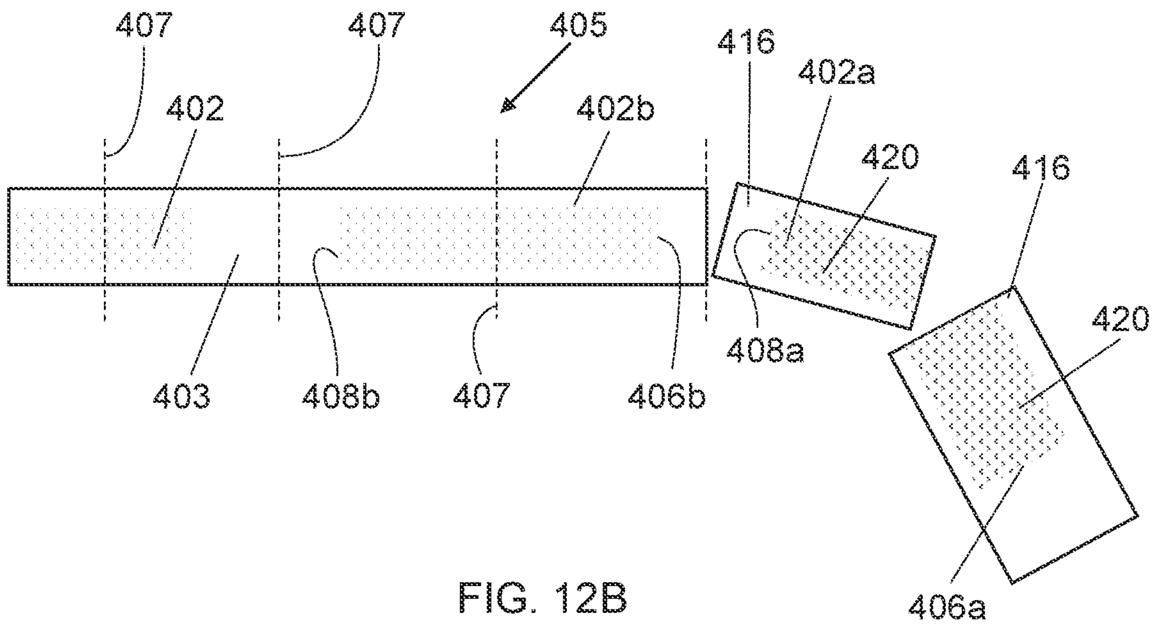
Figure 12C:
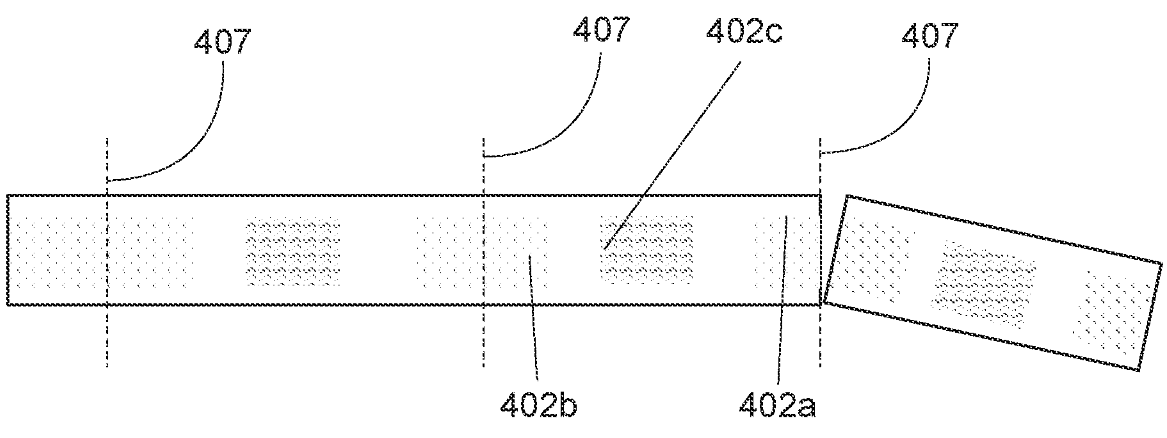

Turning to FIGS. 12A-12C, a method to form fastening members of the present invention comprises providing a web of base substrate material 403, disposing a plurality of engagement portions 402 on the web to form a strip 405 of fastening members. Each of the engagement portions comprises a first transverse edge 406 and a second transverse edge 408 and a plurality of fastening elements 426. The method further comprises cutting the strip of fastening members between the first and second transverse edges 406*a*, 408*a* of a leading engagement portion 402*a* and cutting the strip between the first and second transverse edges 406*ba*, 408*b* of a trailing engagement portion 402*b* to create fastening members 400 each having one or more final engagement portions 420 disposed thereon and an exposed substrate portion 416. The method may further comprise cutting the strip between the second transverse edge of the leading engagement portion 402*a* and the first transverse edge of the trailing fastening member 402*b* as shown in FIG. 12B. The trailing engagement portion 402*b* may immediately following the leading engagement portion 402*a* (FIGS. 12A-12B), or the trailing and leading engagement portions may be separated by one or more intermediate engagement portions 402*c* (FIG. 12C).

Figure 13:
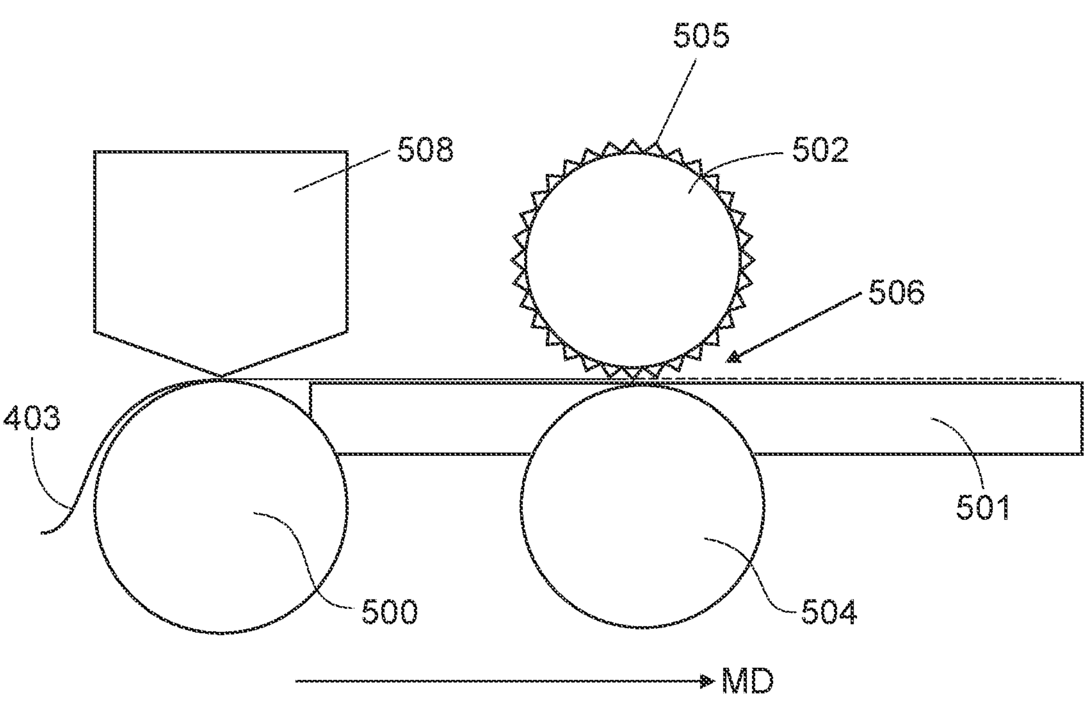
FIG. 13 is a schematic side view of an apparatus for assembling a fastening member according to a nonlimiting embodiment of the present invention.

The web of base substrate material may be conveyed about a roll 500 and/or conveyor belt 501 in a machine direction, MD, as shown in FIG. 13. Likewise, the cutting operation may be performed by one or more blades 505 disposed on a cutting roll 502 operatively engageable with an anvil roll 504 at a nip 506. However, any suitable providing the operation is contemplated, such as a servo driven, pitchless tool.

The web of base substrate material may comprise a web of nonwoven material, a web of film, or a laminate web of nonwoven material and elastomeric material. The web may be formed from constituent materials including formed from one or more polyolefins (e.g., polypropylene, polyethylene), polyester, nylon and combinations thereof.

Figure 14:
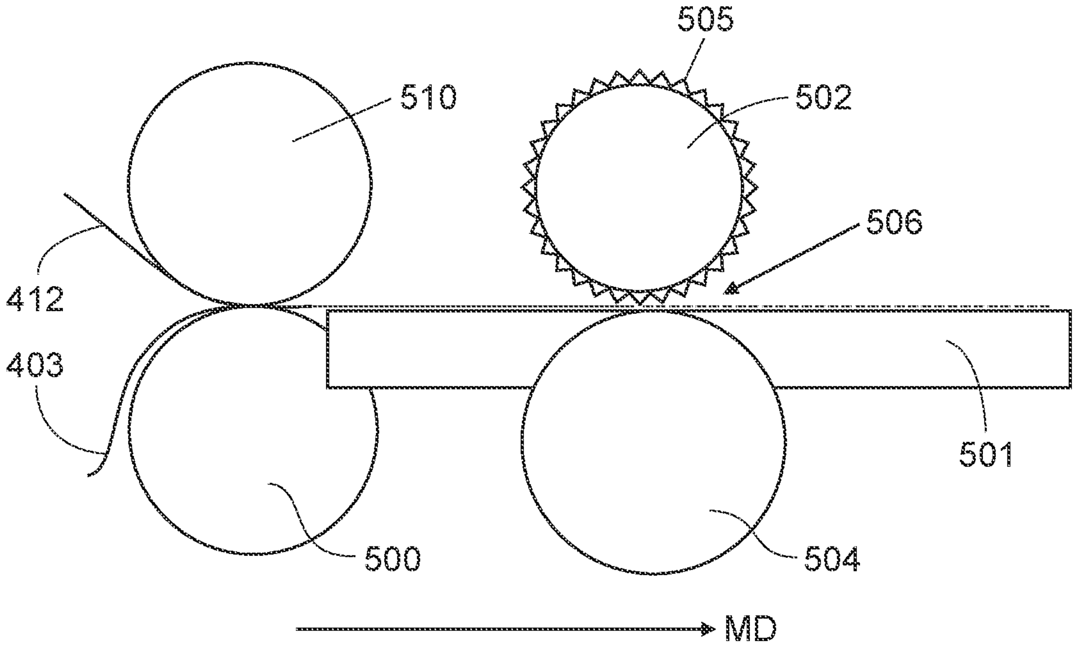
FIG. 14 is a schematic side view of a second apparatus for assembling a fastening member according to a nonlimiting embodiment of the present invention.

In either of the foregoing methods, disposing engagement portion(s) on the web of base substrate material may comprise joining a discrete patch 412 or discrete fastening elements to the web of base substrate material as shown in FIG. 14. The patch may be joined to the web of base substrate material using a bonding roll 510 (or other suitable bonding means). The patch or individual fastening members may be bonded to the web of base substrate material by pressure, adhesive, heat and combinations thereof. Fastening elements may comprise the one or more of the same constituent materials as the web of base substrate material.

The methods may include integrally forming one or more fastening elements from the web of base substrate material by for example softening a portion of the material and pressing it into forming cavities, using for example an ultrasonic horn 508 as shown in FIG. 13. Fastening elements may be formed from one or more layers of the web of base substrate material but from fewer than all layers of the web of base substrate material. The fastening elements may be in the form of hooks. Fastening elements on a fastening member may differ as discussed above.

The final engagement portions may comprise an aggregate width of at least 18 mm and/or the aggregate area of the final engagement portions may be greater than the width of the exposed portion as discussed above. One or more of the final engagement portions may comprise a maximum width of at least 18 mm, a Stiffness of 600 N/m or less, and/or any of the other features disclosed above with respect to engagement portions. The exposed portion may comprise any of the features discussed above with respect to exposed portions. In nonlimiting examples, the area of one or more of the final engagement portions may be greater than the area of the exposed portion and/or the width of one or more of the final engagement portions may be greater than the width of the exposed portion as discussed above. The methods may further include folding each fastening member in the final engagement portion.

Figure 15:
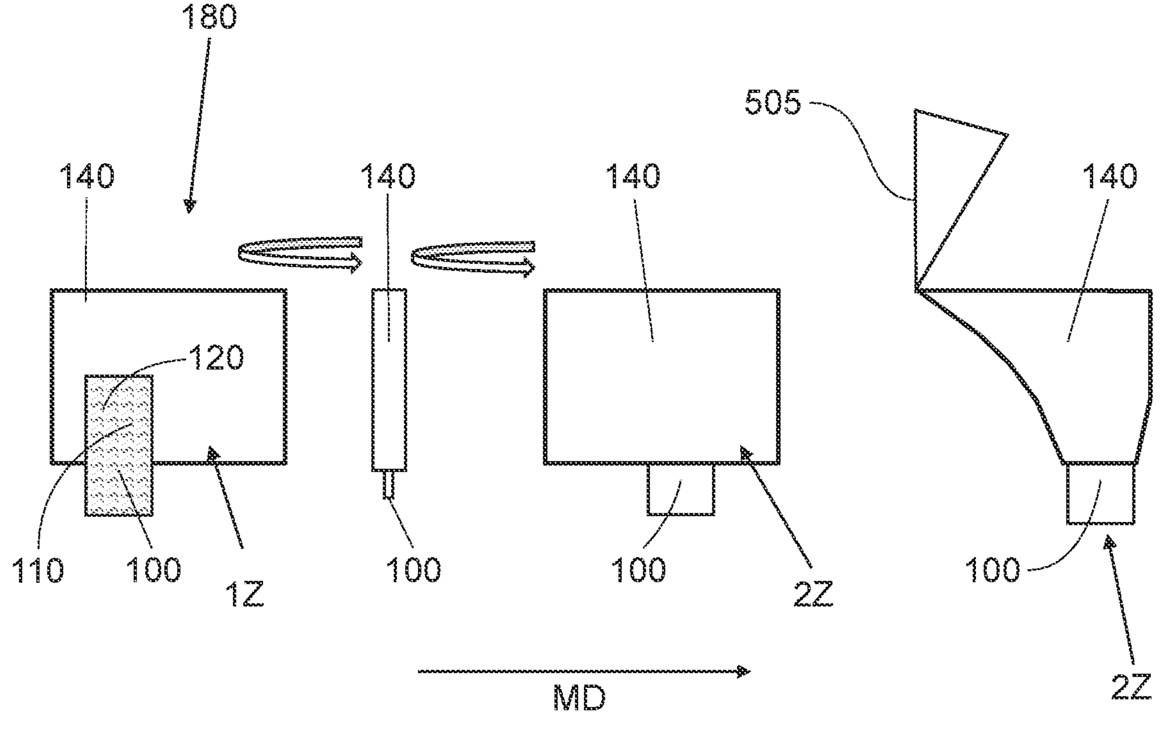
FIG. 15 is a schematic depiction of a fastening member during a converting process.

A method of assembling a fastening member on an absorbent article comprises the steps of providing an absorbent article component 140, providing a fastening member 100 comprising a base substrate 110 and an engagement portion 120 disposed on the base substrate, and attaching the fastening member to the absorbent article in the engagement portion to form a composite 180. The engagement portion comprises one or more fastening elements as discussed above. The fastening elements may comprise one or more of the same constituent material(s) as the base substrate as previously disclosed. The fastening elements may be integrally formed from the base substrate. The method may further include folding the fastening member in the engagement portion. The folding step may occur before or after attaching the fastening member to the absorbent article component. The attaching step may comprise attaching the fastening member to a wearer-facing surface of the absorbent article. The article component may be selected from the group consisting of an ear, a backsheet, a topsheet, a belt or combinations thereof. The fastening member may be attached to the article component to form a composite positioned in a first z-direction orientation, 1Z. The method may comprise turning the composite in the z-direction. The composite may be turned about 170 degrees, or about 180 degrees, or from about 170 to about 190 degrees, reciting for said range every 1 degree increment therein. The composite may be turned to protect the fastening elements from contamination or insult while facilitating other conversions (e.g., bonding, embossing, cutting, printing and the like). For instance, the composite may be turned and the article component may be subsequently trimmed to a desired shape (as shown in FIG. 15), the article component may be joined to another article component, and/or the article component may be printed while in the turned, second z-orientation 2Z. The article component may be attached to the remainder of the absorbent article before or after attaching the fastening member to the article component. Fastening members may be joined to absorbent articles in a waist region.

Leg Gasketing System

Returning to FIG. 1, the absorbent article 10 may comprise a leg gasketing system 70 attached to the chassis 20, which may comprise one or more cuffs. The leg gasketing system may comprise a pair of barrier leg cuffs 72 and one or more leg elastics 55.

Each barrier leg cuff 72 may be formed by a piece of material which is bonded to the absorbent article 10 so it can extend upwards from a wearer-facing surface 9 of the absorbent article 10 and provide improved containment of body exudates approximately at the junction of the torso and legs of the wearer. The barrier leg cuffs 72 are delimited by a proximal edge joined directly or indirectly to the topsheet and/or the backsheet and a free terminal edge 75, which is intended to contact and form a seal with the wearer's skin. The barrier leg cuffs 72 may extend at least partially between the front end edge 13 and the back end edge 19 of the absorbent article 10 on opposite sides of the central longitudinal axis 90 and may be at least present in the crotch region 16. The barrier leg cuffs 72 may each comprise one or more elastics 55 (e.g., elastic strands or strips) near or at the free terminal edge. These elastics 55 cause the barrier leg cuffs 72 to help form a seal around the legs and torso of a wearer. The leg elastics 55 extend at least partially between the front end edge 13 and the back end edge 19. The leg elastics 55 essentially cause portions of the absorbent article 10 proximate to the chassis side edges to help form a seal around the legs of the wearer. The leg elastics 55 may extend at least within the crotch region 16.

In addition to the barrier leg cuffs 72, the article may comprise gasketing cuffs 76, which are joined to the chassis of the absorbent article, in particular to the topsheet 24 and/or the backsheet 26 and are placed externally relative to the barrier leg cuffs 72. The gasketing cuffs 76 may provide a better seal around the thighs of the wearer. A gasketing cuff may comprise a proximal edge and a free terminal edge 77. The free terminal edge 77 may comprise a folded edge. Each gasketing cuff may comprise one or more elastic elements 55 in the chassis of the absorbent article between the topsheet 24 and backsheet 26 in the area of the leg openings. All, or a portion of, the barrier leg cuffs and/or gasketing cuffs may be treated with a lotion or another skin care composition.

Elastic Waist Feature

The absorbent article 10 may comprise at least one elastic waist feature 80 that helps to provide improved fit and containment, as shown in FIG. 1. The elastic waist feature 80 is generally intended to expand and contract to dynamically fit the wearer's waist. Elasticized waist features include waistbands and waist cuffs having pockets formed from a portion of the waist feature 80 that is unattached from the chassis 20. The waist feature may be positioned on the garment-facing surface 11 or the wearer-facing surface 9. Waist features 80 may be joined to the chassis 20 in the first waist region 14 and/or in the second waist region 18. The waist feature can be used in conjunction with the ear 30 to provide desirable stretch and flexibility for proper fit of the article on the wearer. The waist feature may be extensible or elastic in the lateral and/or longitudinal directions.

Test Method

3 Point Bend Test

The bending properties of a sample are measured on a constant rate of extension tensile tester (a suitable instrument is the MTS Alliance using Testworks 4.0 Software or TestSuite Software, as available from MTS Systems Corp., Eden Prairie, MN) using a load cell for which the forces measured are within 1% to 99% of the limit of the cell. All testing is performed in a room controlled at 23° C.±3° C. and 50%±2% relative humidity.

The bottom stationary fixture consists of two bars 3.175 mm in diameter by 60 mm in length, made of polished stainless steel each mounted on its own fork. These 2 bars are mounted horizontally, aligned front to back and parallel to each other, with top radii of the bars vertically aligned. Furthermore, the fixture allows for the two bars to be move horizontally away from each other on a track so that a gap can be set between them while maintaining their orientation. The top fixture consists of a third bar also 3.175 mm in diameter by 60 mm in length, made of polished stainless steel mounted on a fork. When in place the bar of the top fixture is parallel to and aligned front to back with the bars of the bottom fixture. Both fixtures include an integral adapter appropriate to fit the respective position on the tensile tester frame and lock into position such that the bars are orthogonal to the motion of the crossbeam of the tensile tester.

Set the gap between the bars of the lower fixture to 25 mm±0.5 mm (center of bar to center of bar) with the upper bar centered at the midpoint between the lower bars. Set the gage (bottom of top bar to top of lower bars) to 1.0 cm.

Samples are conditioned at 23° C.±3° C. and 50%±2% relative humidity two hours prior to testing. Cut a specimen 50.8 mm in the longitudinal direction of the article (MD) and 50.8 mm in the lateral direction (CD) of the article from the center of the article maintaining their orientation after they are cut. Specimens are taken from an area that is free of folds. Measure the caliper of each specimen, using a digital caliper (e.g. Ono Sokki GS-503 or equivalent) fitted with a 25 mm diameter foot that applies a confining pressure of 0.1 psi. Read the caliper (mm) 5 sec after resting the foot on the sample and record to the nearest 0.01 mm.

Program the tensile tester for a flexural bend test, to move the crosshead such that the top fixture moves down with respect to the lower fixture at a rate of 1.0 mm/sec until the upper bar touches the top surface of the specimen, then continue for an additional 12 mm collecting force (N) and displacement (mm) data at 100 Hz, and return the crosshead to its original gage.

Load a specimen such that it spans the two lower bars centered under the upper bar with its sides parallel to the bars. For the MD orientation, the MD direction is perpendicular to the length of the 3 bars. For the CD orientation, the CD direction is perpendicular to the length of the bars. Zero the crosshead and load cell. Start the run and collect data.

Construct a graph of force (N) verses displacement (m). From the graph, record the maximum peak force to the nearest 1 N/m. In like fashion, repeat the entire test sequence for 3 MD and 3 CD test specimens. Calculate the arithmetic mean of the maximum peak force for the replicates at each orientation (MD and CD) and report as 3 Point Bend Stiffness to the nearest 1 N/m, noting the orientation with the reported value.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fastening member comprising:
- a base substrate;
- one or more engagement portions disposed on the base substrate and comprising a first engagement portion;
- wherein:
  - the engagement portions each comprise;
    - an outboard longitudinal edge;
    - an inboard longitudinal edge;
    - an outboard lateral edge extending between the outboard longitudinal edge and the inboard longitudinal edge;
    - an inboard lateral edge extending between the outboard longitudinal edge and the inboard longitudinal edge; and
    - a plurality of hooks extending between the outboard longitudinal edge and the inboard longitudinal edge and extending between the outboard lateral edge and the inboard lateral edge;
  - the fastening member comprises a fold line;

the fold line is laterally positioned between the outboard longitudinal edge of the first engagement portion and the inboard longitudinal edge of the first engagement portion and is at least partially disposed within the first engagement portion; and at least one engagement portion of the one or more engagement portions comprises one or more hooks integrally formed from the base substrate.

2. The fastening member of claim 1, wherein the one or more engagement portions comprise an aggregate maximum width, $B_A$, that is at least 18 mm.

3. The fastening member of claim 1, wherein the base substrate comprises a base maximum width, A, and wherein the one or more engagement portions comprise an aggregate maximum width, $B_A$, that is at least 70% of the base width, A.

4. The fastening member of claim 1, wherein the fold line is completely disposed within the first engagement portion.

5. The fastening member of claim 1, wherein the base substrate having a first outboard longitudinal edge and a first inboard longitudinal edge and the first engagement portion comprises a second outboard longitudinal edge and a second inboard longitudinal edge, and wherein a maximum distance, D2, between the first outboard longitudinal edge and the second outboard longitudinal edge is 10% or less of the base maximum width, A.

6. The fastening member of claim 1, wherein the first engagement portion comprises a CD Stiffness of 600 N/m or less.

7. The fastening member of claim 1, wherein the one or more engagement portions comprise fastening elements that differ by one of the group consisting of: size, shape, directionality, whether the element is discrete or integral, constituent material, the number and/or type of layers from which integral fastening elements are formed, diameter, height and combinations thereof.

8. An absorbent article comprising a topsheet, backsheet, and absorbent core disposed between the topsheet and backsheet, an ear, and the fastening member of claim 1, wherein the base substrate is joined to a wearer-facing surface of the backsheet, topsheet or ear.

9. A fastening member comprising:

a base substrate having a first outboard longitudinal edge and a first inboard longitudinal edge; and an engagement portion disposed on the base substrate, the engagement portion comprising:

a second outboard longitudinal edge and a second inboard longitudinal edge; and a plurality of fastening elements extending between the second outboard longitudinal edge and the second inboard longitudinal edge;

wherein the first outboard longitudinal edge is at least partially coincident with the second outboard longitudinal edge and the first inboard longitudinal edge is at least partially coincident with the second inboard longitudinal edge;

wherein the first outboard longitudinal edge and the first inboard longitudinal edge are separated by a first lateral edge; and wherein the second outboard longitudinal edge and the second inboard longitudinal edge are separated by a second lateral edge.

10. The fastening member of claim 9, wherein the base substrate comprises a first area and the engagement portion comprises a second area, and wherein the second area is at least 50% of the first area.

11. The fastening member of claim 9, wherein the engagement portion comprises a Stiffness of 600 N/m or less.

12. The fastening member of claim 11, wherein the plurality of fastening elements are integrally formed from the base substrate.

13. The fastening member of claim 9, wherein the fastening elements and the base substrate comprise the same constituent material.

14. The fastening member of claim 9, wherein the engagement portion comprises a length, LE, and wherein first and second longitudinal outboard edges coincide throughout the entire length and/or the first and second longitudinal inboard edges coincide throughout the entire length, LE.

15. The fastening member of claim 9, wherein the base substrate comprises a length, L, and wherein the first and second longitudinal outboard edges coincide through the entire length, L and/or the first and second longitudinal inboard edges coincide through the entire length, L.

16. An absorbent article comprising a topsheet, backsheet and absorbent core disposed between the topsheet and backsheet, and further comprising a back ear and a fastening member;

wherein the fastening member comprises a base substrate having an engagement portion disposed thereon;

wherein the fastening member is joined to the back ear at a fastener attachment bond;

wherein the fastener attachment bond is at least partially disposed in the engagement portion; and wherein the engagement portion comprises:

an outboard longitudinal edge;

an inboard longitudinal edge; and a plurality of fastening elements, wherein the plurality of fastening elements extend between the outboard longitudinal edge and the inboard longitudinal edge.

17. The absorbent article of claim 16, wherein the fastening member is joined to a wearer facing surface of the back ear.

18. The absorbent article of claim 16, wherein the fastening member overlaps the back ear in an overlap zone and comprises a free zone that does not overlap the back ear, wherein the Overlap to Free Area Ratio is 0.1 to 1.

* * * * *